US008879791B2

(12) United States Patent
Drouin et al.

(10) Patent No.: US 8,879,791 B2
(45) Date of Patent: Nov. 4, 2014

(54) METHOD, APPARATUS AND SYSTEM FOR DETERMINING IF A PIECE OF LUGGAGE CONTAINS A LIQUID PRODUCT

(75) Inventors: Stéphane Drouin, Québec (CA); Régis Poulin, Québec (CA); Luc Perron, Charlesbourg (CA); Dan Gudmundson, Québec (CA)

(73) Assignee: Optosecurity Inc., Québec, Québec (CA)

( * ) Notice: Subject to any disclaimer, the term of this patent is extended or adjusted under 35 U.S.C. 154(b) by 338 days.

(21) Appl. No.: 13/387,578

(22) PCT Filed: Jul. 30, 2010

(86) PCT No.: PCT/CA2010/001200
§ 371 (c)(1),
(2), (4) Date: May 3, 2012

(87) PCT Pub. No.: WO2011/011894
PCT Pub. Date: Feb. 3, 2011

(65) Prior Publication Data
US 2012/0275646 A1 Nov. 1, 2012

Related U.S. Application Data

(60) Provisional application No. 61/230,412, filed on Jul. 31, 2009.

(51) Int. Cl.
*G06K 9/00* (2006.01)
*G01N 23/04* (2006.01)
(52) U.S. Cl.
CPC ........ *G01N 23/046* (2013.01); *G01N 2223/637* (2013.01)
USPC ............................................ 382/103; 378/57

(58) Field of Classification Search
CPC .................................. G06K 9/00; G01N 1/00
USPC .......... 382/103, 236; 348/169, 170, 171, 172; 378/46, 57, 66, 87, 90, 92, 98.6, 207; 726/14; 345/424
See application file for complete search history.

(56) References Cited

U.S. PATENT DOCUMENTS 3,342,397 A 9/1967 Duitsman
3,589,511 A 6/1971 Britt
(Continued)

FOREIGN PATENT DOCUMENTS

CA 2574402 1/2006
CA 2623812 5/2007
(Continued)

OTHER PUBLICATIONS

Examiner's Report mailed on Nov. 7, 2012 in connection with European patent application No. 08876865.0, 3 pages.

(Continued)

*Primary Examiner* — Abolfazl Tabatabai

(57) ABSTRACT

A method, an apparatus and a system are provided for determining if a piece of luggage contains a liquid product comprised of a container holding a body of liquid. The piece of luggage is scanned with an X-ray scanner to generate X-ray image data conveying an image of the piece of luggage and contents thereof. The X-ray image data is processed with a computer to detect a liquid product signature in the X-ray image data and determine if a liquid product is present in the piece of luggage. A detection signal is released at an output of the computer conveying whether a liquid product was identified in the piece of luggage. The detection signal may, for example, be used in rendering a visual representation of the piece of luggage on a display device to convey information to an operator as to the presence of a liquid product in the piece of luggage.

40 Claims, 4 Drawing Sheets

(56) References Cited

U.S. PATENT DOCUMENTS

| | | | |
|---|---|---|---|
| 3,609,045 A | 9/1971 | Stein | |
| 3,673,394 A | 6/1972 | Hartmann | |
| 4,392,237 A | 7/1983 | Houston | |
| 4,454,949 A | 6/1984 | Flum | |
| 4,497,065 A | 1/1985 | Tisdale et al. | |
| 4,727,562 A | 2/1988 | Belanger | |
| 4,864,142 A | 9/1989 | Gomberg | |
| 4,870,666 A | 9/1989 | Lonn et al. | |
| 4,962,515 A | 10/1990 | Kopans | |
| 4,974,247 A | 11/1990 | Friddell | |
| 4,985,906 A | 1/1991 | Arnold | |
| 5,027,378 A | 6/1991 | Fujii et al. | |
| 5,044,002 A * | 8/1991 | Stein | 378/54 |
| 5,056,124 A | 10/1991 | Kakimoto et al. | |
| 5,400,381 A | 3/1995 | Steude et al. | |
| 5,428,657 A | 6/1995 | Papanicolopoulos et al. | |
| 5,442,672 A | 8/1995 | Bjorkholm et al. | |
| 5,490,218 A | 2/1996 | Krug et al. | |
| 5,557,108 A | 9/1996 | Tumer | |
| 5,568,262 A | 10/1996 | LaChappelle et al. | |
| 5,600,303 A | 2/1997 | Husseiny et al. | |
| 5,600,700 A * | 2/1997 | Krug et al. | 378/57 |
| 5,692,029 A | 11/1997 | Husseiny et al. | |
| 5,768,334 A | 6/1998 | Maitrejean et al. | |
| 5,838,758 A | 11/1998 | Krug et al. | |
| 5,864,600 A | 1/1999 | Gray et al. | |
| 5,974,111 A | 10/1999 | Krug et al. | |
| 6,018,562 A | 1/2000 | Willson | |
| 6,026,171 A | 2/2000 | Hiraoglu et al. | |
| 6,041,132 A | 3/2000 | Isaacs et al. | |
| 6,054,712 A | 4/2000 | Kormardin et al. | |
| 6,069,936 A | 5/2000 | Bjorkholm | |
| 6,078,642 A | 6/2000 | Simanovsky et al. | |
| 6,175,655 B1 | 1/2001 | George et al. | |
| 6,201,850 B1 | 3/2001 | Heumann | |
| 6,542,574 B2 | 4/2003 | Grodzins | |
| 6,654,445 B2 | 11/2003 | Shepherd et al. | |
| 6,707,381 B1 | 3/2004 | Maloney | |
| 6,707,879 B2 | 3/2004 | McClelland et al. | |
| 6,721,387 B1 | 4/2004 | Naidu et al. | |
| 6,721,391 B2 | 4/2004 | McClelland et al. | |
| 6,753,527 B1 | 6/2004 | Yamagishi et al. | |
| 6,763,083 B2 | 7/2004 | Fernandez | |
| 6,840,120 B2 | 1/2005 | Sakairi et al. | |
| 6,952,163 B2 | 10/2005 | Huey et al. | |
| 7,033,070 B2 | 4/2006 | Azami | |
| 7,065,175 B2 | 6/2006 | Green | |
| 7,092,485 B2 | 8/2006 | Kravis | |
| 7,149,339 B2 | 12/2006 | Veneruso | |
| 7,154,985 B2 | 12/2006 | Dobbs et al. | |
| 7,164,750 B2 | 1/2007 | Nabors et al. | |
| 7,257,188 B2 | 8/2007 | Bjorkholm | |
| 7,260,254 B2 | 8/2007 | Highnam et al. | |
| 7,274,768 B2 | 9/2007 | Green | |
| 7,317,390 B2 | 1/2008 | Huey et al. | |
| 7,355,402 B1 | 4/2008 | Taicher et al. | |
| 7,386,093 B2 | 6/2008 | Wu et al. | |
| 7,508,908 B2 | 3/2009 | Hu et al. | |
| 7,614,788 B2 | 11/2009 | Gatten | |
| 7,684,605 B2 | 3/2010 | Klingenbeck-Regn | |
| 7,727,567 B2 | 6/2010 | Heuft | |
| 7,787,681 B2 | 8/2010 | Zhang et al. | |
| 7,789,401 B2 | 9/2010 | Ambrefe, Jr. | |
| 7,840,360 B1 | 11/2010 | Micheels et al. | |
| 7,869,637 B2 | 1/2011 | Baumgart et al. | |
| 7,873,201 B2 | 1/2011 | Eilbert et al. | |
| 7,945,017 B2 * | 5/2011 | Chen et al. | 378/57 |
| 8,090,150 B2 | 1/2012 | Garms | |
| 8,116,428 B2 | 2/2012 | Gudmundson et al. | |
| 8,150,105 B2 | 4/2012 | Mian et al. | |
| 8,260,020 B2 | 9/2012 | Garms | |
| 2001/0033636 A1 | 10/2001 | Hartick et al. | |
| 2002/0097833 A1 | 7/2002 | Kaiser et al. | |
| 2003/0062373 A1 | 4/2003 | Holland | |
| 2004/0016271 A1 | 1/2004 | Shah et al. | |
| 2004/0101097 A1 | 5/2004 | Wakayama et al. | |
| 2004/0232092 A1 | 11/2004 | Cash | |
| 2004/0252024 A1 | 12/2004 | Huey et al. | |
| 2005/0036689 A1 | 2/2005 | Mahdavieh | |
| 2005/0058242 A1 | 3/2005 | Peschmann | |
| 2005/0078801 A1 | 4/2005 | Georgeson et al. | |
| 2005/0111618 A1 | 5/2005 | Sommer, Jr. et al. | |
| 2005/0117700 A1 | 6/2005 | Peschmann | |
| 2005/0173284 A1 | 8/2005 | Ambrefe, Jr. | |
| 2005/0193648 A1 | 9/2005 | Klein et al. | |
| 2005/0238232 A1 | 10/2005 | Ying et al. | |
| 2006/0022140 A1 | 2/2006 | Connely et al. | |
| 2006/0054682 A1 | 3/2006 | de la Huerga | |
| 2006/0078085 A1 | 4/2006 | Zanker | |
| 2006/0086794 A1 | 4/2006 | Knowles et al. | |
| 2006/0115044 A1 | 6/2006 | Wu et al. | |
| 2006/0133566 A1 | 6/2006 | Li et al. | |
| 2006/0187221 A1 * | 8/2006 | Lakare et al. | 345/424 |
| 2006/0193434 A1 | 8/2006 | Green | |
| 2006/0203960 A1 | 9/2006 | Schlomka et al. | |
| 2006/0239402 A1 | 10/2006 | Hu et al. | |
| 2006/0257005 A1 | 11/2006 | Bergeron et al. | |
| 2007/0003009 A1 | 1/2007 | Gray | |
| 2007/0013519 A1 | 1/2007 | Chung et al. | |
| 2007/0041612 A1 | 2/2007 | Perron et al. | |
| 2007/0041613 A1 | 2/2007 | Perron et al. | |
| 2007/0058037 A1 | 3/2007 | Bergeron et al. | |
| 2007/0098142 A1 | 5/2007 | Rothschild et al. | |
| 2007/0132580 A1 | 6/2007 | Ambrefe, Jr. | |
| 2007/0133743 A1 | 6/2007 | Johnson et al. | |
| 2007/0152033 A1 | 7/2007 | Hind et al. | |
| 2007/0192850 A1 | 8/2007 | Cowburn | |
| 2007/0217571 A1 | 9/2007 | Teslyar et al. | |
| 2007/0297560 A1 | 12/2007 | Song et al. | |
| 2008/0056443 A1 | 3/2008 | Hu et al. | |
| 2008/0062262 A1 | 3/2008 | Perron et al. | |
| 2008/0116267 A1 | 5/2008 | Barber | |
| 2008/0138475 A1 | 6/2008 | Heuft | |
| 2008/0152082 A1 | 6/2008 | Bouchard et al. | |
| 2008/0167552 A1 | 7/2008 | Bouchevreau et al. | |
| 2008/0170660 A1 | 7/2008 | Gudmundson et al. | |
| 2008/0181473 A1 | 7/2008 | Garty et al. | |
| 2008/0240578 A1 | 10/2008 | Gudmundson et al. | |
| 2008/0253627 A1 | 10/2008 | Boyden et al. | |
| 2008/0312768 A1 | 12/2008 | Ewing et al. | |
| 2009/0060135 A1 | 3/2009 | Morton | |
| 2009/0123051 A1 | 5/2009 | Tamai et al. | |
| 2009/0146061 A1 | 6/2009 | Manneschi | |
| 2009/0168963 A1 | 7/2009 | Harding | |
| 2009/0180591 A1 | 7/2009 | Baumgart | |
| 2009/0196396 A1 | 8/2009 | Doyle et al. | |
| 2009/0252295 A1 * | 10/2009 | Foland | 378/98.12 |
| 2010/0027741 A1 | 2/2010 | Doyle et al. | |
| 2010/0074483 A1 | 3/2010 | Janes | |
| 2010/0127169 A1 | 5/2010 | Whittum et al. | |
| 2010/0220910 A1 | 9/2010 | Kaucic et al. | |
| 2010/0284514 A1 | 11/2010 | Zhang et al. | |
| 2010/0329532 A1 | 12/2010 | Masuda et al. | |
| 2011/0007870 A1 | 1/2011 | Roux et al. | |
| 2011/0172972 A1 | 7/2011 | Gudmundson et al. | |
| 2011/0243299 A1 | 10/2011 | Sugita et al. | |
| 2012/0093367 A1 | 4/2012 | Gudmundson et al. | |

FOREIGN PATENT DOCUMENTS

| | | |
|---|---|---|
| CA | 2651728 | 4/2008 |
| CA | 2692662 | 3/2010 |
| CA | 2709468 | 3/2010 |
| CA | 2696031 | 5/2010 |
| CA | 2676913 | 11/2010 |
| CA | 2666838 | 12/2010 |
| CA | 2700553 . | 4/2011 |
| CA | 2690163 | 8/2011 |
| EP | 2189785 | 5/2010 |
| EP | 2696196 | 2/2014 |
| EP | 2331944 | 3/2014 |
| EP | 2334565 | 3/2014 |
| GB | 2420683 | 5/2006 |
| GB | 2441551 | 3/2008 |

(56) References Cited

FOREIGN PATENT DOCUMENTS

| | | |
|---|---|---|
| JP | 2006214725 | 8/2006 |
| WO | WO94/12855 | 6/1994 |
| WO | WO9802763 | 1/1998 |
| WO | WO99/45371 | 9/1999 |
| WO | WO03/052398 | 6/2003 |
| WO | WO 2004/054329 | 6/2004 |
| WO | WO2006/119603 | 11/2006 |
| WO | WO2008/009134 | 1/2008 |
| WO | 2008019473 | 2/2008 |
| WO | WO2008/034232 | 3/2008 |
| WO | WO2008/036456 | 3/2008 |
| WO | WO2008/040119 | 4/2008 |
| WO | WO2008/119151 | 10/2008 |
| WO | WO2009/024818 | 2/2009 |
| WO | WO2009/043145 | 4/2009 |
| WO | WO2009/046529 | 4/2009 |
| WO | WO2009/114928 | 9/2009 |
| WO | WO2009/127353 | 10/2009 |
| WO | WO2010/025538 | 3/2010 |
| WO | WO2010/025539 | 3/2010 |
| WO | WO2010/028474 | 3/2010 |
| WO | WO2010/145016 | 12/2010 |

OTHER PUBLICATIONS

Examiner's Report mailed on Jan. 16, 2013 in connection with Canadian patent application No. 2,697,586, 3 pages.
Examiner's Report mailed on Feb. 4, 2013 in connection with Canadian patent application No. 2,677,439, 2 pages.
Non-Final Office Action issued on Mar. 1, 2013 in connection with U.S. Appl. No. 12/681,826, 32 pages.
Non-Final Office Action issued on Feb. 28, 2013 in connection with U.S. Appl. No. 13/063,869, 52 pages.
Restriction Requirement issued on Mar. 11, 2013 in connection with U.S. Appl. No. 12/680,625, 6 pages.
Notice of intent to grant issued on Apr. 11, 2013 in connection with European patent application No. 08876865.0—5 pages.
Notice of intent to grant issued on May 14, 2013 in connection with European patent application No. 09810945.7—5 pages.
Restriction Requirement issued on Jun. 14, 2013 in connection with U.S. Appl. No. 12/864,988—6 pages.
Examiner's Report mailed on May 29, 2013 in connection with European Patent Application No. 09839849.8—6 pages.
Examiner's Report mailed on Jul. 22, 2013 in connection with Canadian Patent Application 2,737,075—3 pages.
Examiner's Report mailed on Jul. 23, 2013 in connection with Canadian Patent Application 2,677,439—2 pages.
Non-Final Office Action issued on Aug. 14, 2013 in connection with U.S. Appl. No. 12/680,625—9 pages.
Non-Final Office Action issued on Sep. 25, 2013 in connection with U.S. Appl. No. 13/313,635—7 pages.
Non-Final Office Action issued on Oct. 31, 2013 in connection with U.S. Appl. No. 12/864,988—14 pages.
Final Office Action issued on Nov. 14, 2013 in connection with U.S. Appl. No. 13/063,869—50 pages.
Xiang Li et al., "A numerical simulator in VC++on PC for iterative image reconstruction", Journal of X-ray Science and Technology, vol. 11, No. 2, Jan. 1, 2003, pp. 61-70, XP055063644, issn: 0895-3996.
International Search Report mailed on Jan. 10, 2008 in connection with International Patent Application PCT/CA2007/001658, 6 pages.
Written Opinion of the International Searching Authority mailed on Jan. 10, 2008 in connection with International Patent Application PCT/CA2007/001658, 12 pages.
Informal Communication with the Applicant mailed on Sep. 22, 2008 in connection with International Patent Application PCT/CA2007/001658, 4 pages.
International Preliminary Report on Patentability mailed on Dec. 17, 2008 in connection with International Patent Application PCT/CA2007/001658, 7 pages.
International Search Report mailed on Jan. 14, 2008 in connection with International Patent Application PCT/CA2007/001749, 4 pages.
Written Opinion of the International Searching Authority mailed on Jan. 14, 2008 in connection with International Patent Application PCT/CA2007/001749, 4 pages.
International Search Report mailed on Nov. 20, 2008 in connection with International Patent Application PCT/CA2008/001591, 6 pages.
Written Opinion of the International Searching Authority mailed on Nov. 20, 2008 in connection with International Patent Application PCT/CA2008/001591, 6 pages.
International Search Report mailed on Dec. 4, 2008 in connection with International Patent Application PCT/CA2008/001721, 5 pages.
Written Opinion of the International Searching Authority mailed on Dec. 4, 2008 in connection with International Patent Application PCT/CA2008/001721, 5 pages.
International Search Report mailed on Dec. 5, 2008 in connection with International Patent Application PCT/CA2008/001792, 5 pages.
Written Opinion of the International Searching Authority mailed on Dec. 5, 2008 in connection with International Patent Application PCT/CA2008/001792, 5 pages.
International Search Report mailed on Jun. 4, 2009 in connection with International Patent Application PCT/CA2008/002025, 5 pages.
Written Opinion of the International Searching Authority mailed on Jun. 4, 2009 in connection with International Patent Application PCT/CA2008/002025, 6 pages.
International Search Report mailed on Jul. 6, 2009 in connection with International Patent Application PCT/CA2009/000395, 4 pages.
Written Opinion of the International Searching Authority mailed on Jul. 6, 2009 in connection with International Patent Application PCT/CA2009/000395, 4 pages.
International Search Report mailed on Aug. 6, 2009 in connection with International Patent Application PCT/CA2009/000401, 4 pages.
Written Opinion of the International Searching Authority mailed on Aug. 6, 2009 in connection with International Patent Application PCT/CA2009/000401, 8 pages.
International Search Report mailed on Nov. 10, 2009 in connection with International Patent Application PCT/CA2009/000811, 7 pages.
Written Opinion of the International Searching Authority mailed on Nov. 10, 2009 in connection with International Patent Application PCT/CA2009/000811, 3 pages.
International Preliminary Report on Patentability mailed on Feb. 1, 2010 in connection with International Patent Application PCT/CA2008/001792, 3 pages.
International Preliminary Report on Patentability mailed on Apr. 15, 2010 in connection with International Patent Application PCT/CA2008/001721, 6 pages.
Written Opinion of the International Searching Authority mailed on Sep. 22, 2010 in connection with International Patent Application PCT/CA2010/000916, 6 pages.
International Search Report mailed on Sep. 22, 2010 in connection with International Patent Application PCT/CA2010/000916, 4 pages.
International Preliminary Report on Patentability mailed on Sep. 21, 2010 in connection with International Patent Application PCT/CA2008/001591, 7 pages.
Written Opinion of the International Searching Authority mailed on Nov. 19, 2010 in connection with International Patent Application PCT/CA2010/001200, 6 pages.
International Search Report mailed on Nov. 19, 2010 in connection with International Patent Application PCT/CA2010/001200, 5 pages.
International Preliminary Report on Patentability mailed on Jan. 12, 2011 in connection with International Patent Application PCT/CA2009/000401, 15 pages.
International Preliminary Report on Patentability mailed on Oct. 24, 2011 in connection with International Patent Application PCT/CA2010/000916, 17 pages.
Office Action mailed on Jul. 29, 2009 in connection with Canadian Patent Application 2,651,728, 6 pages.
Office Action mailed on Jul. 10, 2009 in connection with Canadian Patent Application 2,666,838, 3 pages.
Office Action mailed on Nov. 3, 2009 in connection with Canadian Patent Application 2,666,838, 5 pages.
Office Action mailed on Jan. 28, 2010 in connection with Canadian Patent Application 2,676,913, 2 pages.

(56) References Cited

OTHER PUBLICATIONS

Office Action mailed on Jan. 28, 2010 in connection with Canadian Patent Application 2,666,838, 5 pages.
Office Action mailed on Mar. 2, 2010 in connection with Canadian Patent Application 2,676,903 4 pages.
Office Action mailed on Mar. 19, 2010 in connection with Canadian Patent Application 2,651,728 2 pages.
Office Action mailed on Mar. 31, 2010 in connection with Canadian Patent Application 2,690,163—3 pages.
Office Action mailed on May 5, 2010 in connection with Canadian Patent Application 2,676,913—2 pages.
Office Action mailed on May 14, 2010 in connection with Canadian Patent Application 2,690,831—3 pages.
Office Action mailed on Jun. 7, 2010 in connection with Canadian Patent Application 2,692,662—3 pages.
Office Action mailed on Jun. 30, 2010 in connection with Canadian patent application 2,696,031—2 pages.
Office Action mailed on Jun. 28, 2010 in connection with Canadian patent application 2,697,525—3 pages.
Office Action mailed on Aug. 5, 2010 in connection with U.S. Appl. No. 12/385,253—18 pages.
Office Action mailed on Aug. 12, 2010 in connection with U.S. Appl. No. 12/311,522—17 pages.
Office Action mailed on Aug. 31, 2010 in connection with Canadian patent application 2,690,831—2 pages.
Office Action mailed on Aug. 31, 2010 in connection with Canadian patent application 2,692,662—3 pages.
Office Action mailed on Sep. 30, 2010 in connection with U.S. Appl. No. 12/311,031—8 pages.
Office Action mailed on Oct. 6, 2010 in connection with Canadian patent application 2,696,031—2 pages.
Office Action mailed on Oct. 29, 2010 in connection with Canadian Patent Application 2,651,728—6 pages.
Office Action mailed on Oct. 28, 2010 in connection with Canadian Patent Application 2,676,903—2 pages.
Search Report mailed on Feb. 17, 2012 in connection with European Patent Application No. 08835738.9—7 pages.
Search Report mailed on Feb. 1, 2012 in connection with European Patent Application No. 08876865.0—7 pages.
Search Report mailed on Jul. 18, 2012 in connection with European Patent Application No. 09839849.8—8 pages.
Examiner's Report mailed on Jul. 18, 2012 in connection with European Patent Application No. 09810945.7—4 pages.
Examiner's Report mailed on Aug. 31, 2012 in connection with European patent application No. 2007815851.6—6 pages.
Bottigli et al., "Voxel-based Monte Carlo Simulation of X-Ray imaging and spectroscopy experiments", Spectrochimia Acta. Part B: Atomic Spectroscopy, vol. 59, No. 10-11—Oct. 8, 2004, pp. 1747-1754, XP004598270.
Sluser M et al., "Model-based probabilistic relaxation segmentation applied to threat detection in airport x-ray imagery", Electrical and Computer Engineering, 1999 IEEE Canadian Conference on Edmonton, Alta., Canada, May 9 to May 12, 1999, pp. 720-726, vol. 2, XP032158352.
Office Action mailed on Nov. 2, 2010 in connection with Canadian Patent Application 2,690,163—1 page.
Office Action mailed on Nov. 17, 2010 in connection with Canadian Patent Application 2,709,468—2 pages.
Examiner's Report mailed on Jan. 31, 2011 in connection with Canadian Patent Application 2,697,525—2 pages.
Office Action mailed on Feb. 10, 2011 in connection with U.S. Appl. No. 12/680,622—10 pages.
Office Action mailed on Feb. 8, 2011 in connection with U.S. Appl. No. 12/385,253—14 pages.
Office Action mailed on Feb. 9, 2011 in connection with U.S. Appl. No. 12/311,522—11 pages.
Office Action mailed on Mar. 2, 2011 in connection with U.S. Appl. No. 12/311,031—9 pages.
Examiner's Report mailed on Mar. 29, 2011 in connection with Canadian Patent Application 2,725,626—5 pages.
Examiner's Report mailed on Mar. 29, 2011 in connection with Canadian Patent Application 2,690,831—2 pages.
Office Action mailed on Apr. 20, 2011 in connection with U.S. Appl. No. 12/311,031—20 pages.
Examiner's Report mailed on May 2, 2011 in connection with Canadian patent application 2,692,662—3 pages.
European Search Report mailed on Jun. 9, 2011 in connection with European patent application No. EP2007815851.6—6 Pages.
Notice of allowance mailed on May 5, 2011 in connection with U.S. Appl. No. 12/385,253—8 pages.
Notice of allowance mailed on May 6, 2011 in connection with U.S. Appl. No. 12/311,522—7 pages.
Notice of allowance mailed on May 6, 2011 in connection with U.S. Appl. No. 12/680,622—8 pages.
Examiner's Report mailed on Jul. 5, 2011 in connection with Canadian patent application 2,696,031—2 pages.
Examiner's Report issued on Jul. 19, 2011 in connection with Canadian patent application 2,651,728—2 pages.
Examiner's Report mailed on Aug. 10, 2011 in connection with Canadian Patent Application 2,725,626—4 pages.
Examiner's Report mailed on Sep. 2, 2011 in connection with Canadian Patent Application 2,737,075—3 pages.
Notice of allowance mailed on Sep. 15, 2011 in connection with U.S. Appl. No. 12/311,031.
Benjamin, R., "Object-Based 3D X-Ray Imaging for Second-line Security Screening", London, 1995, (Abstract).
PinPoint TM Threat Identification Software, http://www.guardiantechintl.com/security.php?npage=pinpoint, Jul. 25, 2005, 4 pages.
"Secure Flight Passenger Screening Program", http://www.globalsecurity.org/security/systems/passenger_screen.htm, Oct. 28, 2005, 6 pages.
OPTOSECURITY, "Security Technology Overview: Advanced Vehicle Verification & Threat Identification", 1 page.
Airport Magazine, Solutions, Products, Services, vol. 7, Mar. 2006, 5 pages.
Page, D. L. et al., "Perception-based 3D Triangle Mesh Segmentation Using Fast Marching Watersheds.", Proc. Intl. Conf. on Computer Vision and Pattern Recognition, vol. II, pp. 27-32, Madison, WI, Jun. 2003.
Freud et al., "Simulation of X-ray NDT Imaging Techniques", Proceedings of the 15th World Conference on Non-Destructive Testing, Rome, Oct. 15-21, 2000, http://www.ndt.net/article/wcndt00/papers/idn256/idn256.htm, pages consulted on Dec. 3, 2009, 7 pages.
Gao et al., "Application of X-ray CT to liquid security inspection: System analysys and beam hardening correction", Nuclear Instruments & Methods in Physics Research, Section—A:Accelerators, Spectrometers, Detectors and Associated Equipement, Elsevier, Amsterdam, NL, vol. 579, No. 1, pp. 395-399, Aug. 8, 2007.
Xie et al., "Simulation of X-ray Imaging Systems for Luggage Inspection", Second Explosives Detection Symposium and Aviation Security Conference, Nov. 12-15, 1996, pp. 248-253.
U.S. Statutory Invention Registration No. H2001 H—Newman, Oct. 5, 2004.
International Preliminary Report on Patentability mailed on Nov. 22, 2011 in connection with International Patent Application PCT/CA2010/001200, 12 pages.
Dreisetel, Pia et al. "Detection of liquid explosives using tomosynthetic reconstruction in multiview dual-energy x-ray systems",1st EU Conference on the Detection of Explosives, held in Avignon, France, from Mar. 14th to 16th, 2011.
Search Report mailed on Oct. 7, 2011 in connection with European Patent Application No. 09810945.7—7 pages.
Notice of Allowance issued on Dec. 2, 2013 in connection with U.S. Appl. No. 12/680,625—10 pages.
Extended European Search Report issued on Dec. 18, 2013 in connection with European patent application No. 13191619.9—6 pages.
Notice of Allowance issued on Jan. 16, 2014 in connection with U.S. Appl. No. 13/313,635—10 pages.
Notice of Allowance issued on Feb. 21, 2014 in connection with U.S. Appl. No. 12/864,988—7 pages.

(56) References Cited

OTHER PUBLICATIONS

European Search Report mailed on Apr. 14, 2014 in connection with Europeant Patent Application No. 10788557.6—8 pages.
Examiner's Report mailed on Aug. 5, 2014 in connection with Canadian Patent Application No. 2,737,075—3 pages.
Restriction Requirement issued on Sep. 11, 2014 in connection with U.S. Appl. No. 14/244,213—6 pages.
Non-final Office Action issued on Aug. 13, 2014 in connection with U.S. Appl. No. 13/377,872—19 pages.
Examiner's Report mailed on Jul. 15, 2014 in connection with Canadian Patent Application No. 2,677,439—2 pages.
Examiner's Report mailed on Jul. 9, 2014 in connection with European Patent Application No. 09839849.8—3 pages.
Examiner's Report mailed on Jun. 26, 2014 in connection with European Patent Application No. 07815851.6—4 pages.

* cited by examiner

METHOD, APPARATUS AND SYSTEM FOR DETERMINING IF A PIECE OF LUGGAGE CONTAINS A LIQUID PRODUCT

CROSS REFERENCE TO RELATED APPLICATIONS

This application is a national stage application under 35 U.S.C. 371 of PCT Application No. PCT/CA2010/001200 having an international filing date of 30 Jul. 2010, which designated the United States, which PCT application claimed the benefit of U.S. Provisional Application No. 61/230,412 filed 31 Jul. 2009, the entire disclosure of each of which is incorporated herein by reference.

FIELD OF THE INVENTION

The present invention relates to technologies for use identifying the presence of a liquid product inside a receptacle. The invention has numerous applications, in particular it can be used for scanning hand carried baggage at security check points, for example but not limited to airport and train security checkpoints.

BACKGROUND OF THE INVENTION

Some liquids or combinations of liquids and other compounds may cause enough damage to bring down an aircraft. As no reliable technology-based solution currently exists to adequately address this threat, authorities have implemented a ban of most liquids, gels and aerosols in cabin baggage.

As a result, there have been disruptions in operations (e.g., a longer screening process; changed the focus for screeners; additional line-ups), major inconveniences for passengers (as well as potential health hazards for some) and economic concerns (e.g., increased screening costs; lost revenues for airlines and duty free shops; large quantities of confiscated—including hazardous—merchandise to dispose of), and so on.

Clearly, there is a need to provide a technology-based solution to address the threat of fluids that are flammable, explosive or commonly used as ingredients in explosive or incendiary devices.

SUMMARY OF THE INVENTION

In accordance with a first aspect, the invention provides a method for determining if a piece of luggage contains a liquid product, the liquid product being comprised of a container holding a body of liquid. The method comprises receiving X-ray image data conveying an image of the piece of luggage and contents thereof, the X-ray image data being generated by scanning the luggage with an X-ray scanner. The method also comprises processing the X-ray image data with a computer to detect a signature of the liquid product in the X-ray image data and determine if a liquid product is present in the piece of luggage. The method also comprises releasing at an output of the computer a detection signal conveying a result obtained by processing the X-ray image data.

In accordance with a specific example of implementation, the detection signal indicates whether a liquid product has been identified in the piece of luggage. The detection signal may also include location information conveying a location in the piece of luggage where a liquid product has been identified. Optionally, the detection signal conveys confidence information indicative of a level of confidence that a portion of the X-ray image represents a liquid product.

In accordance with a specific example of implementation, processing the X-ray image data includes identifying a set of areas in the image conveyed by the X-ray image data as candidates for containing at least a portion of a liquid product. In accordance with a specific example, processing the X-ray image data may also include processing the areas in the identified set of areas based in part on a set of qualifying factors in order to derive a subset of the set of areas. The set of qualifying factors may include one or more factors such as, for example, size of area, symmetry of area, Zeff of area, edge characteristics of area, gray level of area and aspect ratio of area.

In accordance with a specific example of implementation, processing the X-ray image data includes processing the areas in the set of areas according to a set of rejection criterion in order to derive a subset of the set of areas, the set of rejection criterion allowing identifying areas in the set of areas that are unlikely to be associated to a portion of a liquid product. The set of rejection criterion includes one or more rejection criterion. Non-limiting examples of rejection criterion include, without being limited to information related to a geometry, information related to density. The set of rejection criterion may also include information conveying signatures of articles that register as false positives.

In accordance with a specific example of implementation, processing the X-ray image data includes processing the areas in the set of areas according to a set of merging criterion to determine whether some of the areas in the set of areas can be combined to form a merged area.

In accordance with a specific example of implementation, the X-ray image data is obtained using a multi-view X-ray scanner and the image of the piece of luggage and contents thereof is a first X-ray image obtained by subjecting the piece of luggage to X-rays in a first orientation. The X-ray image data conveys a second X-ray image of the piece of luggage, the second image being obtained by subjecting the luggage item to X-rays in a second orientation.

In accordance with another aspect, the invention provides a computer readable storage medium storing a program element suitable for execution by a computing apparatus for determining if a piece of luggage contains a liquid product in accordance with the above described method.

In accordance with another broad aspect, the invention provides an apparatus suitable for determining if a piece of luggage contains a liquid product in accordance with the above described method.

In accordance with another aspect, the invention provides a system suitable for determining if a piece of luggage contains a liquid product, the liquid product being comprised of a container holding a body of liquid. The system comprises an inspection device for performing an X-ray inspection on the product using penetrating radiation to generate X-ray image data associated with the product under inspection. The system also comprises an apparatus for determining if the piece of luggage contains a liquid product in accordance with the above described method. The system also comprises a display screen in communication with the apparatus for visually conveying to an operator information related to a presence of a liquid product in the piece of luggage, the information conveyed to the operator being based on information released by the apparatus.

In accordance with another broad aspect, the invention provides a method for determining if a piece of luggage contains a liquid product, the liquid product being comprised of a container holding a body of liquid. The method comprises receiving X-ray image data conveying an image of the piece of luggage, the X-ray image data being generated by scanning the luggage with an X-ray scanner. The method also comprises processing the X-ray image data with a computer to detect a signature of the liquid product in the X-ray image data and determine if a liquid product is present in the piece of luggage. The method also comprises generating a detection signal conveying whether a liquid product has been identified in the piece of luggage. The method also comprises rendering a visual representation of the piece of luggage on a display to convey information to an operator related to a detected liquid product in the piece of luggage, the visual representation of the piece of luggage being derived at least in part based on the X-ray image data and the detection signal.

In accordance with another aspect, the invention provides a computer readable storage medium storing a program element suitable for execution by a computing apparatus for determining if a piece of luggage contains a liquid product in accordance with the above described method.

In accordance with another broad aspect, the invention provides an apparatus suitable for determining if a piece of luggage contains a liquid product in accordance with the above described method.

In accordance with another aspect, the invention provides a system suitable for determining if a piece of luggage contains a liquid product, the liquid product being comprised of a container holding a body of liquid. The system comprises an inspection device for performing an X-ray inspection on the product using penetrating radiation to generate X-ray image data associated with the product under inspection. The system also comprises an apparatus for determining if the piece of luggage contains a liquid product in accordance with the above described method. The system also comprises a display screen in communication with the apparatus for visually conveying to an operator information related to a presence of a liquid product in the piece of luggage, the information conveyed to the operator being based on information released by the apparatus.

In accordance with a specific example of information, the visual representation of the piece of luggage conveys a location in the piece of luggage corresponding to a detected liquid product. In a non-limited example of implementation, the location in the piece of luggage corresponding to the detected liquid product is conveyed by highlighting a portion of the visual representation of the piece of luggage.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

A detailed description of examples of implementation of the present invention is provided hereinbelow with reference to the following drawings, in which.

Figure 1:
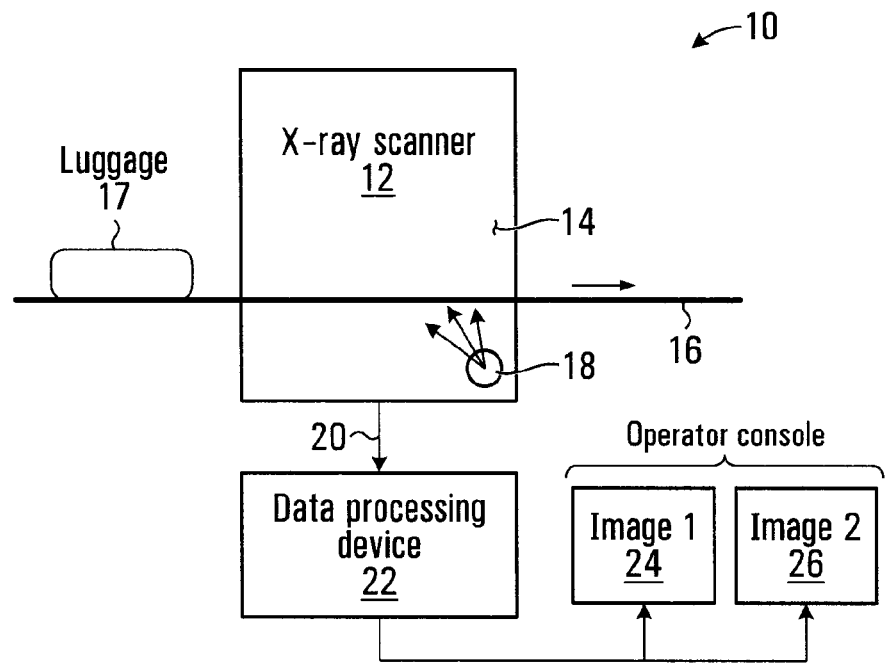
FIG. 1 is a block diagram, illustrating at a high level a system for identifying the presence of a liquid product in a piece of luggage, according to a non-limiting example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

FIG. 1 is a high level block diagram of an X-ray scanning system that can be used to determine automatically if a piece of luggage contains a liquid product. A liquid is comprised of a container, such as a bottle made of glass, plastic, metal or any other material holding a liquid. For the purpose of the present specification "liquid" refers to a state of matter that is neither gas nor solid and that generally takes the shape of the container in which it is put. This definition would, therefore encompass substances that are pastes or gels, in addition to substances having a characteristic readiness to flow. For instance, toothpaste, and other materials having the consistency of toothpaste and that take the shape of the container in which they are put are considered to fall in the definition of "liquid".

The X-ray scanning system 10 includes an X-ray scanner 12 having a X-ray scanning area 14 in which objects to be scanned are carried by a conveyor belt 16. In the specific example of implementation of the invention, the X-ray scanning system 10 is used for scanning luggage 17, such as suitcases, bags or any other container used to store the belongings of a traveler. Accordingly, the X-ray scanning system 10 can be used at security checkpoints such as at airports to determine if the piece of luggage holds liquid products.

The X-ray scanner 12 has a source of X-ray radiation 18, which typically would be located under the conveyor belt 16 which generates X-rays toward the object to be scanned, namely the luggage 17. The X-rays interact with the contents of the luggage, including the liquid product. X-ray detectors (not-shown) in the drawings capture the X-rays subsequent to the interaction and generate an X-ray image signal that encodes the interaction.

The X-ray scanner 12 can be a single view apparatus or a multi-view apparatus. A single view apparatus is an apparatus that generates X-ray image data of the luggage 17 from one perspective (view). Typically, a single view apparatus has a single radiation source which represents the point of view from which the X-ray image data is produced. A multi-view apparatus provides an X-ray image data that depicts the luggage 17 from two or more perspectives. In a specific example, the perspectives are orthogonal to one another, such as a bottom view and a side view. In this instance, several radiation sources are used, one for each view. It is also possible to provide a third view, in order to create a three-dimensional X-ray image that shows the luggage 17 from three sides.

Note that while the present specification uses an X-ray scanner as an example to perform the detection of the liquid product in the luggage 17, other types of penetrating radiation can also be considered for performing the scanning operation.

Irrespective of the number of views that the X-ray scanning device 12 uses, it outputs X-ray image data at an output 20. The X-ray image data is digital information that encodes the interaction between the X-rays and the contents of the luggage 17. The particular data format or communication protocol is not critical for the success of the invention and many different possibilities exist in this regard, without departing from the spirit of the invention.

A data processing apparatus 22 is connected to the output and receives the X-ray image data and processes the X-ray image data in order to determine if the luggage 17 contains a liquid product. The data processing apparatus 22 generates on the basis of the image processing operation that it performed detection information that indicates if a liquid product has been identified in the luggage 17. The detection information can be conveyed in a number of possible ways. In one simple example, the detection information can trigger an alarm that simply indicates to a human operator that a liquid product has been identified in the luggage 17. The alarm can be visual or oral. In a different possibility, the detection information can be embedded into an image signal used to drive a display device at the operator console to show an image of the luggage 17. The image is generated on the basis of the X-ray image data. One or more individual images can be shown on the display device. In the example illustrated in FIG. 1, the display device has two individual monitors 24, 26 where each individual monitor 24, 26 shows a different image of the luggage 17, such as a different view of the luggage 17 when the X-ray scanner 12 is a multi-view apparatus. The detection information can be depicted on the display device in conjunction with the image of the luggage.

For instance, the detection information is such as to inform the operator that a liquid product has been identified and also provides location information indicating the location of the liquid product in the luggage 17. The location information may be conveyed by highlighting the portion of the X-ray image that depicts the liquid product. Examples of highlighting include drawing the outline of the portion of the X-ray image that depicts the liquid product with a contrasting color, filling the entire portion of the X-ray image of interest with a pattern of color, generating a mark that on the image that visually draws the attention of the observer or de-emphasizing the other areas of the X-ray image such that only the portion of interest is clear and visible. When a mark is being inserted in the image, the mark can be an arrow, a circle or any other geometric figure drawn adjacent the X-ray image portion of interest.

When two or more images of the luggage 17 are rendered on the monitors 24, 26 the detection information has multiple components, one for each set of image data associated to a particular view of the luggage 17. In a multi-view X-ray scanning system 10 context, the detection information conveyed by the image data designates in each image the presence and the location of the liquid product. In this fashion, both images of the luggage 17 show to the operator the location of the liquid product in the respective view. When the monitor 24 is set to illustrate a front view of the luggage 17, the detection information will highlight a portion of the X-ray image showing liquid product as it would appear when the luggage is looked at from the front. Similarly, the monitor 26 will show a side view of the luggage 17, the liquid product being highlighted to show how it would appear when the luggage 17 is seen from that perspective. This provides the operator with the ability to build a mental image of the internal contents of the luggage 17 in order to better appreciate the location of the liquid product relative to other items in the luggage 17 and also to validate the results of the detection process, namely that the highlighted areas are indeed different views of a liquid product and not of something else.

The detection information can also be used as an input to a secondary processing stage that is designed to automatically determine if the liquid in the liquid product is licit or illicit. The detection information supplied to the secondary processing indicates how the liquid interacts with X-rays which can be used to determine if the liquid is licit or illicit. In a specific example, the detection information may simply be the pixels that are within the boundary of the liquid product outline identified in the X-ray image data. Those pixels are analyzed by the secondary processing stage to determine if the liquid product is licit or illicit. What constitutes a licit product or an illicit may differ depending on the application. In a security screening context, a liquid product that may explode, is corrosive or flammable would typically be considered 'illicit'. For cargo inspection applications, certain categories of products may be considered illicit such as alcohol, for instance.

Figure 2:
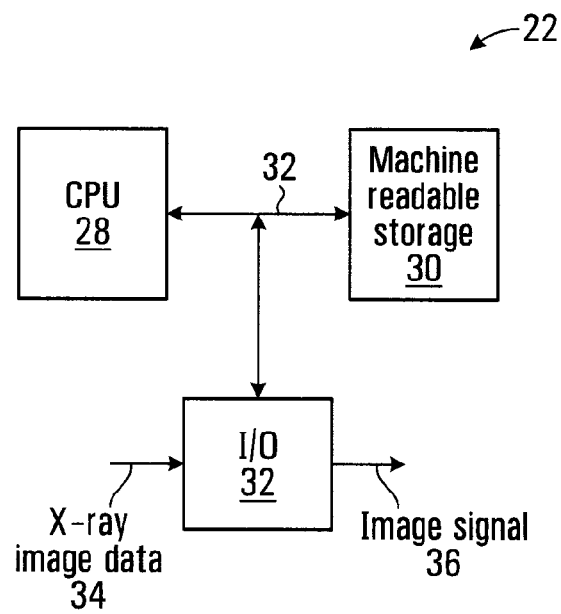
FIG. 2 is a block diagram of a data processing module that is a component of the system shown in FIG. 1.

FIG. 2 is a more detailed block diagram of the data processing device 22. The data processing device is essentially a computing platform that has a Central Processing Unit (CPU) 28, a machine readable storage 30 connected to the CPU 28 via a data bus 32 and an Input/Output (I/O) interface 32. The machine readable storage is encoded with software that performs the analysis of the image data output from the X-ray scanner 12. The machine readable storage may be implemented on a variety of different devices that are capable of storing data. The I/O 32 is the interface that receives external signals which in turn are processed by the software and also outputs the data that conveys the results of the processing. In the example described, the X-ray image data is generated at the output 20 of the X-ray scanner 12 is input at the I/O 32 at 34. The detection information generated by the data processing device 22 is output from the I/O 32 and it is conveyed in an image signal driving the monitors 24, 26.

Figure 3:
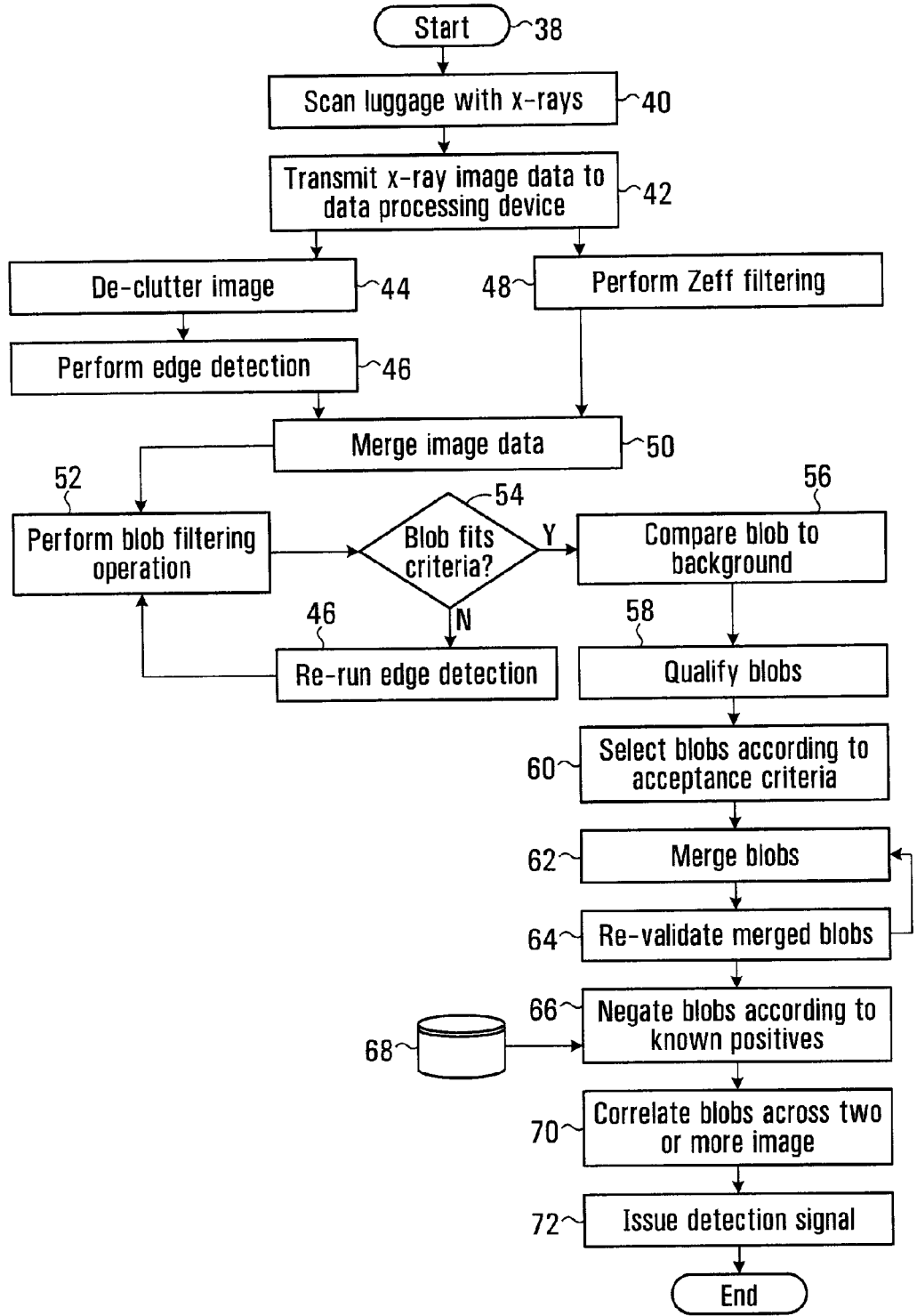
FIG. 3 is a flowchart that illustrates the process of a liquid product detection software executed by the data processing module shown in FIG. 2.

FIG. 3 is a flowchart that illustrates the general operation of the software as it is being executed by the CPU 28. For completeness, the flowchart also illustrates some additional steps that are not directly implemented by the software.

The process starts at step 38, followed by step 40 at which the X-ray scanner 12 performs a scan of the luggage 17. This step assumes that the luggage 17 has been previously transported by the conveyor belt 16 in the scanning area 14. The X-ray scan generates X-ray image data that can be single view X-ray image data or multi-view X-ray image data as discussed earlier.

At step 42, the X-ray image data is transmitted to the data processing device 22 via the I/O 32. The X-ray image data is then stored in the machine readable storage 30 and it is ready for processing.

At step 44, a first processing thread is initiated. The X-ray image data is de-cluttered in order to remove from the image or to reduce the presence in the image of areas that are contrasting with neighboring areas. The specific purpose is to entirely remove or reduce the presence in image areas that potentially represent liquid products elements that are associated with another article which overlays the liquid product in the luggage 17. An example would be a clothes hanger that overlaps with the liquid product. The clothes hanger is made of metal that attenuates X-rays much more than the liquid product and would then clearly contrast with the liquid product image. Another example is an electrical wire that overlaps with the liquid product. The different X-ray attenuation characteristics of these articles will show in the image very clearly.

Figure 4:
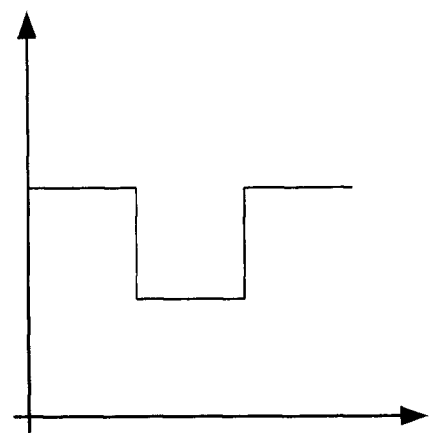
FIG. 4 is graph of a bottom-hat filter.

For image processing purposes it is generally desirable to "morph" the smaller component with the larger background (the liquid product) in order to obtain a more uniform image in which the smaller component will be less apparent. Different types of algorithms can be used to perform image de-cluttering. One such algorithm is the so called "bottom-hat filter". FIG. 4 is a graph of a bottom-hat filter. The bottom-hat filter is a rectangle function. Its name is related to the shape of the filter which looks like an inverted hat. In use, the filter operates by adjusting the pixel gray scale level of each pixel according to the gray scale level of neighboring pixels. This has the effect of smoothing the image. Note that the adjustment of the pixel gray scale level can be weighted towards the a certain Zeff range, such that areas that display an attenuation level which is substantially different from an area corresponding to liquid are altered more toward that Zeff range than other areas that manifest a smaller delta. The degree to which the image is "de-cluttered" can vary but in general care should be taken not to de-clutter to the point where relevant image information is lost. Also note that de-cluttering algorithms other than a bottom hat algorithm can be used without departing from the sprit of the invention.

The de-cluttered image is processed at step 46 to perform edge detection. The purpose is to identify in the X-ray image data areas of the image that might be components of a liquid product and to define their edges. The output of this operation is a series of image areas ("blobs") along with a definition of their boundaries. A boundary is considered to be a sharp and cleanly visible change in the X-ray image data attenuation values. The process uses programmable settings for what is considered to be a "sharp change". Step 46 performs in fact a first pass operation that uses looser settings intended to capture anything that might be a boundary in the image. A second, tighter pass will be performed later, as it will be discussed below. The identification of blobs uses two assumptions; (1) the Zeff of a liquid product follows a predetermined Zeff variation pattern, in particular it is constant or varies at a slow rate. Therefore, locally Zeff changes little or not at all. (2) the image of the liquid product is bound by a visible edge in the image.

A watershed segmentation algorithm can be used for this step. The algorithm starts on seed regions in the image and grows these regions progressively until a sharp continuous boundary is found. The growth process is performed progressively. A blob is grown to encompass candidate pixels in the image when the processing determines that the Zeff variance between the Zeff values of the candidate pixels and adjacent pixels that are already part of the blob, is less than a predetermined amount. The Zeff variance is a configurable range that is typically set in the range from 0.1 to 1.0. The growth process stops when a continuous boundary is encountered where the Zeff variance exceeds the limit.

Therefore, this operation produces a preliminary blob map that essentially segments the X-ray image into blobs and defines their respective boundaries.

A second processing thread is initiated with step 48 which processes the X-ray image data as received from the data processing device 22 in order to perform a Zeff filtering on the pixels in order to discard pixels that are obviously not liquids. This operation is based on the assumption that the Zeff of a liquid varies in a predetermined range and anything that is outside of this range is not a liquid. Accordingly, processing step 48 examines individually the pixels of the X-ray image data to retain only those that fall in the predetermined (but configurable) range. In a specific example of implementation, the Zeff estimate for a liquid is set in the range of about 6.0 to about 15.5. Therefore, areas of the image with Zeff estimates less than 6 or more than 15.5 are considered to represent materials other than liquids and are discarded.

The output of the processing step 48 is therefore a Zeff map which retains only the image areas that can potentially represent liquids.

Processing step 50 receives the blob map and filters the blob map on the basis of the Zeff map. The purpose of this operation is to discard the blobs that have a Zeff estimate which is outside the range associated with a liquid.

Step 52 performs a series of additional filtering operations that rely on geometric features of liquid products in order to disqualify blobs that are not likely to represent a liquid product or a component of a liquid product. The following filtering operations are being performed:
 1. Size—the size of each blob is assessed and only blobs having sizes in the range of 1000 to 15,000 pixels are retained. Note that this is a configurable parameter which can be changed according to the specific application. Blobs that are smaller than 1000 pixels are discarded while blobs that are larger than 15,000 pixels are marked for further processing. The rationale is that blobs less than 1000 pixels are considered too small for further processing; accordingly they are no longer useful. However, blobs that are larger than 15,000 pixels are not permanently discarded on the basis that an exceedingly large blob may in fact be made up of two or more smaller blobs that need to be separated.
 2. Poor solidity—The solidity of a blob is parameter that determines the clustering or distribution of the pixels in the blob. More specifically, the solidity of the blob is the area of the blob divided by the area of its convex hull. For example, a perfectly circular blob has a solidity of 1.0. A blob that has the shape of a pen, namely a slender elongated body will have solidity of significantly less than 1. Bottle shapes typically have a solidity which is high and this assumption is used to discard blobs that are not likely to represent a bottle. Examples of solidity thresholds that can be used to discriminate the blobs include a solidity of more than 0.5, preferably more than 0.7 and even more preferably more than 0.8.
 3. Aspect ratio—The aspect ratio is the ratio between the length and the width of the blob. The processing therefore determines for each blob two maximal dimension axes that are orthogonal and computes the aspect ratio. Here, the assumption is that bottles have an aspect ratio within a certain range and anything that is outside this range is not likely to be a bottle. Examples of aspect ratio thresholds that can be used include values between about 10 and about 1.

If the processing operation at step 46 has identified blobs that exceed the allowable size range, namely in excess of 15,000 pixels, which is determined by conditional step 54, edge detection step 46 is run one more time but with the Zeff variance threshold set at a tighter level in an attempt to break-up the larger blobs into smaller ones. This operation may be run iteratively several times with increasingly tighter variance levels. The number of variations can vary. In a specific example of implementation, they have been set to 2. If the operation breaks up the large blobs into smaller ones then processing returns back to step 52 that will filter the newly found blobs on the basis of size, solidity and aspect ratio. At this time, if exceedingly large blobs still remain, they are permanently discarded.

At step 56, the remaining blobs are compared to the background to see if they meet a minimum differentiation factor. In this example, the differentiation is a difference in X-ray attenuation between the blob and the background of the blob that is the area adjacent the blob boundary. This process assumes that in the luggage, the liquid product is overlapping with some other article. As such the X-ray image of the luggage conveys, in the area of the blob compound attenuation information, namely attenuation due to the liquid body in the liquid product and also attenuation due to the article that overlaps with the liquid body. However, outside of the blob, the liquid body no longer contributes to the attenuation and the attenuation is likely due only to the article. For the blob to represent a liquid body, the difference in X-ray attenuation between the blob and its background has to meet certain criteria. First the blob must convey more X-ray attenuation than the background area and not less. Secondly, the level of differentiation in X-ray attenuation should exceed a certain threshold. In a specific example of implementation, this threshold is set to the minimal degree of X-ray attenuation of a liquid body can manifest in practice. For instance, the benchmark that can be used is acetone, which is a liquid that attenuates X-rays to a lesser extent than other liquids which may be encountered in a security screening context. As such, the differentiation threshold is set to the X-ray attenuation value that a bottle of acetone manifests. The thickness of the bottle, which corresponds to the length of a path taken by an X-ray through the bottle, may be estimated in a number of different manners. In a specific example of implementation, the thickness of the bottle is set to a minimum reasonable thickness given the width of the blob. In a non-limiting example, the thickness of the bottle is estimated to the width of the blob divided by three. In this non-limiting example the bottle is assumed to have a generally elliptical cross-section and the width of the blob corresponds to the semi-major axis of the ellipse. The division by three is simply a value selected based on an assumption that it would be somewhat unlikely for an elliptical bottle have a ratio between its semi-major axis and semi-minor axis to be greater than three. It is however to be understand that alternative examples of implementation may make use of different approaches for estimating the path length for use in the calculation of the X-ray attenuation value.

If the degree of X-ray attenuation differentiation is less than the minimal threshold the blob is disqualified.

Figure 5:
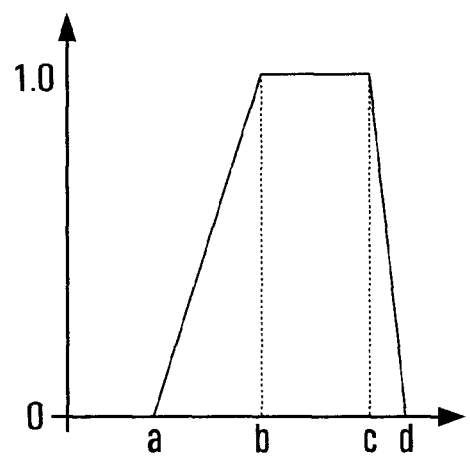
FIG. 5 is a graph of a trapezoidal function for performing a fuzzy logic processing operation.

At step 58, the remaining blobs in the X-ray image data are compared to one another in order to qualify them in terms of likelihood of representing a liquid product or a portion of a liquid product. The purpose in ranking the blobs is to be able to select the top one or several blobs that have ranked higher than the others as likely portions of the image representing one or more liquid products. The blobs are qualified by using a fuzzy logic process on the basis of several factors. The fuzzy logic process is a thresholding operation using a trapezoidal function, shown in FIG. 5 is characterized by four thresholds a, b, c, and d. All values below a or above d receive a membership value of 0; all values above b and below c receive a membership of 1, while the values in the range from a to b and from c to d receive a membership in the range from 1 to 0, depending on their position with respect to the thresholds. Examples of individual factors that can be considered are discussed below:

1. Area—The surface area of each blob is computed by counting the number of pixels included in the convex hull of the blob. The convex hull is used as an estimate of the bottle size which also provides dome tolerance to occlusion and border segmentation issues. In one example, threshold values for a, b, c, and d for evaluating $F_{area}$, are 0, 0, 56666, and 65535, in terms of number of pixels.
2. Blob solidity—As discussed earlier the blob solidity is determined by computing the area of blob and dividing it by the area of its convex hull.

In one example, threshold values for a, b, c, and d for evaluating $F_{so}$, are 0, 0.833, 0.888, and 1.0. Actual liquid products have a solidity that is close to the maximum value. In the specific example provided, unless the solidity is above 0.8333 the solidity factor for the candidate receives a membership of 0.

3. Blob symmetry—Since a typical liquid product has a high degree of symmetry, whether the liquid product is seen from the side, from the top, from the bottom or from any intermediate side, the symmetry factor is relevant for ranking blobs. The symmetry of a blob is computed by an algorithm which operates by drawing candidate symmetry axes through the blob and determines which axis provides the "best fit". For each candidate axis, the algorithm computes the distribution of pixels in the blob, on each axis side. The best fit axis is the one for which the most uniform pixel distribution can be achieved. The degree of symmetry is expressed by a symmetry factor that has a numerical value in the range of 1.0 to 0.0 A blob that has shape which is perfectly symmetrical about a certain axis will have a symmetry factor of 1. In one example, threshold values for a, b, c, and d for evaluating $F_{sy}$, are 0, 0.944, 1.0, and 1.0. Actual liquid products have a symmetry that is close to the maximum value.
4. Blob width—Since the width of typical liquid products falls in a certain range, blobs having width dimensions outside this range are less likely to represent liquid products than blobs with width dimensions within the range. The width of a blob is determined by fitting around the blob a rectangle and then measuring the minimum size of the rectangle. In one example, threshold values for a, b, c, and d for evaluating $F_{sy}$, on images taken with an X-ray scanner manufactured by Rapiscan Systems, model Rapiscan 620 DVAT (Dual View Advanced Technology) are 0, 32.2, 54.4, and 65535, in terms of pixels. These values are only examples and for other machines they may vary.
5. Robust Zeff Average—An estimate of the Zeff across the entire blob is computed by estimating the median value of the Zeff values computed in connection with all the pixels in each blob. Through experimentation it has been found that the Zeff of a bottle is typically lower than 11.11. In one example, threshold values for a, b, c, and d for evaluating $F_{rz}$, are 0, 0, 11.11 and 18.22.
6. Inside edge magnitude average—Each blob is processed to determine the extent of "edges" that can be seen inside the blob. The lower the magnitude of image features suggesting "edges" the better since ideally the liquid body should offer a smooth image. The inside edge factor is computed by using a 3 pixel by 3 pixel edge finding kernel, known in the art. The kernel processes the pixels of the blob and computes an average edge magnitude. For images taken with the Rapiscan 620 DVAT X-ray scanner, which are 16 bits per pixel images, in has been found through experimentation that the average inside edge magnitude is lower than 500 for blobs representing liquid products. In one example, threshold values for a, b, c, and d for evaluating $F_{ie}$, are 0, 0, 500 and 9277.78.
7. Gray level average—Through experimentation is has been found that the average gray level inside a blob that represents a liquid product is typically less than a certain threshold. For 16 bits per pixel images taken with a Rapiscan 620 DVAT X-ray scanner, the threshold is in the area of 14,000 and more specifically less than 13677. Thus examples of the threshold values for computing $F_g$, could be 0, 0, 13667 and 65535.
8. Aspect ratio—the aspect ratio of the blob was used earlier in order to disqualify blobs that are highly unlikely to represent liquid products, however that same factor can also be used to rank blobs in terms of likelihood. Examples of aspect ratio thresholds that can be used include values between about 10 and about 1.

The next step of the process is to compute for each blob a confidence score. The confidence score is the product of fuzzy memberships, for instance $$\text{Confidence}=100.0 \times F_d \times F_{so} \times F_{sy} \times F_w \times F_{rz} \times F_{ie} \times F_g$$

Note that the factors listed above are examples only. They are not all required in all cases and other factors can also be used.

Processing step 60 ranks the blobs based on the confidence level computed at the previous step and performs a selection of the blobs that are likely liquid products. In a specific example of implementation a blob is a likely liquid product when the confidence level of the blob is above a certain threshold, which may vary depending on the system tolerance for false positives. A typical setting for the threshold is 80%, in other words every blob that has a confidence level in excess of this threshold is considered to represent a liquid product or a component of a liquid product.

Figure 6:
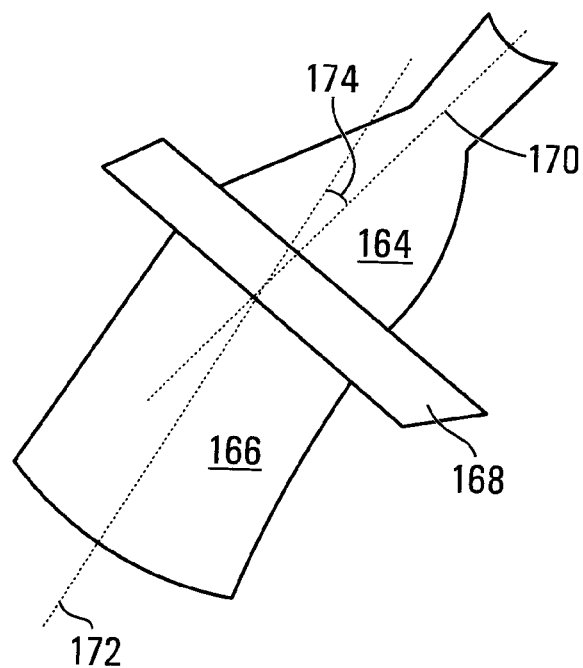
FIG. 6 shows an image of a liquid product when the liquid product is partially obstructed by another object.

The processing now continues with step 62 that will attempt to merge certain blobs which in reality may be different portions of the same liquid product. A liquid product may show in the X-ray image data as two blobs when an object "obscures" partially the liquid product, hence it appears in the X-ray image data as two blobs separated from one another. This is shown at FIG. 6. The simplified X-ray image shows a first blob 164, a second blob 166 and an object 168 that separates the blobs 164 and 166. This image is produced when an object in the luggage 17 overlaps with the liquid product. For instance, the object 168 may be made of metallic material, hence it attenuates X-ray more than the liquid product. During the processing operation, the blobs 164 and 166 are identified as separate blobs because of the interference by the object 168, however in reality they are part of the same liquid product.

The merge operation attempts to find blobs that have similar characteristics and that logically would be parts of the same liquid product. Examples of characteristics that can be used in order to merge blobs include:

1. Distance—If blobs are parts of the same bottle they cannot be too far apart. Accordingly, the software will measure the distance between all blob pairs in order to find possible candidates. If the blobs in a certain pair are separated by a distance that exceeds a threshold the software labels disqualifies this pair for merging. In a specific example, threshold is set to the sum of the square root of the area of the first blob and the square root of the area of the second blob. The candidate pairs that remain are further processed as per the following factors.
2. Zeff similarity—the blobs in each candidate pair are evaluated in terms of Zeff similarity. If the Zeff is very similar in both blobs, the likelihood of the blobs being part of the same liquid product increases. In a non-limiting example, the amount of similarity is determined by generating Zeff values distribution curves (bell curve) for each blob and by comparing these to see the extent to which they overlap.
3. Symmetry—if two blobs have similar symmetry axes this is a further indication that they are part of the same liquid product. Consider the example of FIG. 6, in which the symmetry axes 170, 172 for each blob 164, 166 have been computed and drawn. A factor in assessing the similitude in the symmetry is the angle 174 defined between the axes; the lower the angle the higher the similitude.
4. Resulting solidity—the solidity factor of the combined blobs is re-computed to determine if it tends toward typical values associated with a liquid product or tends away from it. If it tends toward it, this is yet a further indication that the blobs are part of the same liquid product.
5. Gray level intensity—the gray level intensity of each blob is compared to determine if they are similar. Again, a threshold can be used here—if the gray level intensity similitude is above a certain level the blobs are likely to be part of the same liquid product.
6. Size—the total area of the merged blocks cannot exceed the maximum allowable size for liquid products. In other words, the merged blobs should not collective define an area that is too large to be a liquid product. An example of maximal total area is 15,000 pixels when the Rapiscan 620 DVAT X-ray scanner is being used.

In making a decision on whether the blobs in the pair are part of the same liquid product, a fuzzy logic function, similar to the one described earlier can be used which takes into account the different factors above and computes a confidence level. Above a certain percentage, say 80% the system assumes that the blobs are in fact parts of the same liquid product and logically associates them.

Note that the blob merging operation can be run multiple times in an iterative fashion. If the first iteration successfully merges a pair of blobs, the operation is run again to see if another pair can be merged. In this fashion, images of liquid products that are highly fragmented into multiple blobs can be merged one pair of blobs at the time.

If the blob merging operation at step 62 has merged two or more blobs, then processing step 64 is initiated which re-computes the confidence value. Since the blobs have changed then the confidence factor that was attributed before the merge to the respective blobs may no longer be valid. A new confidence computation is then performed by following the steps discussed earlier.

At step 66 the blobs that are considered to be likely liquid products will be processed against signatures of known positives in order to further reduce the likelihood of incorrect results. The false positives are objects that are typically found in a luggage and share some of the features of a liquid product. The false positives filtering may be done on a number of factors, such as geometry and density among others. A database 68, which in practice may be part of the machine readable storage 30, contains signatures of articles that may register as false positives. The signatures may be related to the geometry of the article or may be related to the material that it is made from or possibly both. The step 66 will receive data from the database 68 which conveys the signature information and processes the X-ray image data at the areas where blobs have been identified as likely liquid products. The processing searches for the signatures and if any such signature is identified in the X-ray image, then the blob is disqualified as a false positive. Examples of articles that may register as liquid products include:

1. CD's. CD's have characteristic geometric shapes and Zeff that are analogous to the shape and Zeff of a liquid product in the X-ray image. Accordingly, the previous processing steps may not succeed in filtering out these objects. In order to remove them the software searches the blobs for geometric features that are characteristic of a CD but not likely to appear in the case of a liquid product. One such geometric feature is a circular aperture in the center of the CD. Since the circular aperture is of a standard dimension, the software processes the edges of the blobs using a known image processing algorithm, to determine if anyone of the edges or edge portions manifests a similar geometry. Another possibility in connection with CD's, using the material signature approach is to consider the Zeff variation pattern from the center to the periphery. In the case of a CD, the Zeff is likely to be constant while in the case of a liquid product, which when seen from the bottom looks round and is similar to a CD, will manifest a Zeff profile that varies from the center to the periphery. Anyone of those factors, either alone or in combination can be used to disqualify blobs in the image.

2. Shoes. A shoe may appear in the X-ray image as a liquid product because it has a shape that resembles a liquid product, especially when the sole of the shoe is apparent in the image. A shoe sole has a geometric form that is similar to the shape of a liquid product namely in terms of symmetry. To filter out shoes, a technique that works best relies on material properties namely density. The density of a shoe is significantly less than the density of a liquid. Accordingly, the processing will derive from the X-ray image data an estimate of the density of the material in the blob area of the X-ray image and will compare it to a threshold to determine if it is too low to be a liquid.

3. Books and binders. Books and binders can be identified by the presence a very even Zeff distribution over the entire area of the blob. Accordingly, the processing will derive from the X-ray image data the Zeff in the blob area and will determine the amount of variation throughout that area. If the amount of variation is below a certain minim threshold of variation, the blob is considered as potentially corresponding to a book or a binder and unlikely to be a liquid product. Books and binders can also be identified by the presence of blob have a generally large square surface. Accordingly, the processing will determine if the shape of the blob is generally square and whether the area of the blob exceeds a certain maximum area. If the shape of the blob is generally square and if the size of the area of the blob exceeds a certain threshold size, the blob is considered as potentially corresponding to a book or a binder and unlikely to be a liquid product.

Accordingly, the output of step 66 is a further refined list of blobs from which known positives have been removed.

Processing step 70 is invoked when the X-ray scanner 12 has a multi view scanning capability. In such case, the X-ray scanner 12 generates multiple X-ray images of the luggage, where each image has the potential to show a liquid product that may be present in the luggage. Accordingly, additional confidence can be gained in the results of the processing operation to identify liquid products in the luggage, when the results are consistent across the entire image set. In other words, if a liquid product is identified in one of the images and a liquid product is also identified in one of the images then the likelihood of the identification being correct increases.

When multiple views of the luggage are present, the X-ray data from each view is processed independently as described earlier. The X-ray image data of each view is subjected to steps 42 to 66 to produce a list, associated with that particular view which indicates if a liquid product has been detected in the image and also providing characterizing information in connection with the liquid product, such as its location in the image along with the results of the processing performed to reach the conclusion.

The results for each view are then correlated to determine if they match. The correlation operation may involve the following steps that can be implemented individually or in combination:

1. In the context of a dual view X-ray scanner 12 which produces two images of the luggage 17 from views that intersect with one another (although not necessarily positioned at 90° from one another), the process determines if there is a geometric correlation between the position of a blob determined to be a liquid product in the first image and the position of a blob also determined to be a liquid product in the second image. The correlation is relatively simple to do since many of the multi-view commercially available X-ray scanners 12 output with the X-ray image data image alignment information that allows correlating areas of one image with areas of another image. For instance, and as it known to persons skilled in the art, an X-ray image produced by the X-ray scanner 12 is made up by a succession of columns, where each column is output by the linear detector array. In the case of a dual-view X-ray scanner (or scanners have more than two views), the columns between the X-ray images match, such that it is possible to determine for each column in one image the corresponding column in the other image. As such, if a liquid product is identified on one of the images, and its location is determined to span a certain number of image columns, then a correlation would be deemed to exist if a liquid product is also found in the other image over the same image column set. Different strategies can be used to alter the confidence level depending on whether a correlation between the images exists. One such strategy is to increase the level of confidence for each liquid product identified in one image for which a correlation exists in the other image. However, if no correlation is found for a particular liquid product one possibility is to reduce the confidence level. Another possibility is to leave the confidence level unchanged to account for the possibility that in a particular view the liquid product is obscured and not detectable.

2. In addition to performing inter-image correlation it is possible to use the position information derived from the two or more images in order to perform additional verifications to disqualify outcomes that are physically impossible or simply inconsistent with the geometry of the X-ray scanner 12 or the luggage 17. In the case of a dual-view X-ray scanner, a positive correlation of a liquid product between the two X-ray images can be used to define a space in which the liquid product resides. This space is essentially a three dimensional space (since two views are available) which can be used to determine if the liquid can possibly exist at that location. For instance if this three dimensional space is located outside the boundaries of the luggage, the results are disqualified since the liquid product cannot possibly reside outside the luggage.

3. The correlation operation may also involve comparing Zeff values obtained for blobs in different views to determine whether blobs from different views are sufficiently similar to another to be considered a potential match.

At step 72, the detection signal is issued which indicates if the luggage 17 contains a liquid product and the location of the liquid product in the luggage 17. As discussed previously, the detection signal can be embedded in an image signal that shows to the operator the X-ray image of the suitcase, emphasizing the area of the image where the liquid product is located. Another possibility is to use the detection signal to initiate another processing operation which determines on the basis of the information conveyed by the X-ray image data if the liquid product is licit or illicit. In other words, in addition to determining if a liquid product is present in the luggage, the system additionally will determine the status of the liquid in terms of threat or legality. In this particular case, the detection signal will implicitly be conveyed by the results of the status assessment. For example, if the operator is notified that a dangerous liquid is present in the luggage, then it follows that a positive detection of a liquid product in the luggage has occurred.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A method for performing security screening on luggage, the method comprising:
   a) receiving X-ray image data conveying an image of a piece of luggage and contents thereof, the X-ray image data being generated by scanning the piece of luggage with an X-ray scanner;
   b) processing the X-ray image data using program code executed by a computer to detect if a liquid product is present in the piece of luggage, the liquid product being comprised of a container holding a body of liquid, wherein processing the X-ray image data includes using the program code executed by the computer to detect a liquid product signature in the X-ray image data;
   c) releasing at an output of the computer detection results obtained by processing the X-ray image data.

2. A method as defined in claim 1, wherein processing the X-ray image data includes identifying in the image conveyed by the X-ray image data an area of interest.

3. A method as defined in claim 2, comprising:
   a) processing the X-ray image data to estimate a thickness of the identified area of interest;
   b) selectively disqualifying the identified area of interest as being unlikely to be associated with the liquid product at least in part by processing the estimated thickness of the identified area of interest in combination with attenuation information derived from the X-ray image data.

4. A method as defined in claim 2, comprising:
   i. processing the X-ray image data to derive geometric information associated with the identified area of interest;
   ii. selectively disqualifying the identified area of interest for being unlikely to be associated with the liquid product at least in part based on the derived geometric information.

5. A method as defined in claim 4, comprising selectively disqualifying the identified area of interest for being unlikely to be associated with the liquid product at least in part based on:
   a) the derived geometric information; and
   b) a threshold aspect ratio.

6. A method as defined in claim 4, comprising selectively disqualifying the identified area of interest for being unlikely to be associated with the liquid product at least in part based on:
   a) the derived geometric information; and
   b) a reference solidity threshold.

7. A method as defined in claim 2, comprising selectively disqualifying the identified area of interest for being unlikely to be associated with the liquid product at least in part based on symmetrical properties of the identified area of interest.

8. A method as defined in claim 2, comprising:
   i. processing the identified area of interest to derive density information associated with the identified area of interest;
   ii. selectively disqualifying the identified area of interest for being unlikely to be associated with the liquid product at least in part based on the derived density information.

9. A method as defined in claim 2, comprising:
   (1) processing the identified area of interest to determine whether it is likely to be associated with at least one object in a set of imposter objects;
   (2) selectively disqualifying the identified area of interest for being unlikely to be associated with the liquid product at least in part based on results obtained in (1).

10. A method as defined in claim 9, wherein the set of imposter objects includes at least one object selected from the set consisting of CDs, Shoes, books and binders.

11. A method as defined in claim 2, wherein identifying the area of interest includes:
   a) deriving compensated X-ray image data at least in part by compensating the X-ray image data for an amount of object induced X-ray attenuation resulting from X-rays travelling through an object in the piece of luggage, the object being unlikely to be part of the liquid product;
   b) using the compensated X-ray image data when identifying the area of interest in the image.

12. A method as defined in claim 2, wherein identifying the area of interest includes identifying in the image conveyed by the X-ray image data a set of areas of interest.

13. A method as defined in claim 12, comprising processing at least some of the identified areas of interest according to a set of merging criterion to determine whether two or more areas of interest can be combined to form a merged area of interest.

14. A method as defined in claim 1 wherein the detection results convey a location in the piece of luggage corresponding to the liquid product.

15. A method as defined in claim 1, said method comprising rendering a visual representation of the piece of luggage, the visual representation of the piece of luggage being derived at least in part based on the X-ray image data and the detection results and conveying to an operator a location in the piece of luggage corresponding to the liquid product.

16. A method as defined in claim 15, wherein the location in the piece of luggage corresponding to the liquid product is conveyed by highlighting a portion of the visual representation of the piece of luggage.

17. A method as defined in claim 1, wherein the X-ray image data is obtained using a multi-view X-ray scanner and wherein said image of the piece of luggage and contents thereof is a first X-ray image obtained by subjecting the piece of luggage to X-rays in a first orientation, said X-ray image data conveying a second X-ray image of the piece of luggage, the second image being obtained by subjecting the piece of luggage item to X-rays in a second orientation.

18. A method as defined in claim 17, comprising processing the first X-ray image and the second X-ray image to derive the detection results.

19. A non-transitory computer readable storage medium storing a program element suitable for execution by a computing apparatus for use in performing security screening on luggage, said computing apparatus comprising:
   a) a memory unit;
   b) a processor operatively connected to said memory unit, said program element when executing on said processor being configured for:
      i. receiving X-ray image data conveying an image of a piece of luggage and contents thereof, the X-ray image data being generated by scanning the piece of luggage with an X-ray scanner;

ii. processing the X-ray image data to detect if a liquid product is present in the piece of luggage, the liquid product being comprised of a container holding a body of liquid, wherein processing the X-ray image data includes detecting a liquid product signature in the X-ray image data;

iii. releasing detection results obtained by processing the X-ray image data.

20. A non-transitory computer readable storage medium as defined in claim 19, wherein processing the X-ray image data includes identifying in the image conveyed by the X-ray image data an area of interest.

21. A non-transitory computer readable storage medium as defined in claim 20, wherein said program element when executing on said processor is configured for:
   a) processing the X-ray image data to estimate a thickness of the identified area of interest;
   b) selectively disqualifying the identified area of interest as being unlikely to be associated with the liquid product at least in part by processing the estimated thickness of the identified area of interest in combination with attenuation information derived from the X-ray image data.

22. A non-transitory computer readable storage medium as defined in claim 20, wherein said program element when executing on said processor is configured for:
   i. processing the X-ray image data to derive geometric information associated with the identified area of interest;
   ii. selectively disqualifying the identified area of interest for being unlikely to be associated with the liquid product at least in part based on the derived geometric information.

23. A non-transitory computer readable storage medium as defined in claim 20, wherein said program element when executing on said processor is configured for:
   i. processing the identified area of interest to derive density information associated with the identified area of interest;
   ii. selectively disqualifying the identified area of interest for being unlikely to be associated with the liquid product at least in part based on the derived density information.

24. A non-transitory computer readable storage medium as defined in claim 20, wherein said program element when executing on said processor is configured for:
   (1) processing the identified area of interest to determine whether it is likely to be associated with at least one object in a set of imposter objects;
   (2) selectively disqualifying the identified area of interest for being unlikely to be associated with the liquid product at least in part based on results obtained in (1).

25. A non-transitory computer readable storage medium as defined in claim 24, wherein the set of imposter objects includes at least one object selected from the set consisting of CDs, Shoes, books and binders.

26. A non-transitory computer readable storage medium as defined in claim 20, wherein identifying the area of interest includes:
   a) deriving compensated X-ray image data at least in part by compensating the X-ray image data for an amount of object induced X-ray attenuation resulting from X-rays travelling through an object in the piece of luggage, the object being unlikely to be part of the liquid product;
   b) using the compensated X-ray image data when identifying the area of interest in the image.

27. A non-transitory computer readable storage medium as defined in claim 19, wherein said program element when executing on said processor is configured for rendering a visual representation of the piece of luggage, the visual representation of the piece of luggage being derived at least in part based on the X-ray image data and the detection results and conveying to an operator a location in the piece of luggage corresponding to the liquid product.

28. A non-transitory computer readable storage medium as defined in claim 27, wherein the location in the piece of luggage corresponding to the liquid product is conveyed by highlighting a portion of the visual representation of the piece of luggage.

29. An apparatus for use in performing security screening on luggage, said apparatus comprising:
   a) an input for receiving X-ray image data conveying an image of a piece of luggage and contents thereof, the X-ray image data being generated by scanning the piece of luggage with an X-ray scanner;
   b) a processing unit programmed for processing the X-ray image data received at the input to detect if a liquid product is present in the piece of luggage, the liquid product being comprised of a container holding a body of liquid, wherein processing the X-ray image data includes detecting a liquid product signature in the X-ray image data;
   c) an output for releasing detection results obtained by the processing unit.

30. An apparatus as defined in claim 29, wherein processing the X-ray image data includes identifying in the image conveyed by the X-ray image data an area of interest.

31. An apparatus as defined in claim 30, wherein said processing unit is further programmed for:
   a) processing the X-ray image data to estimate a thickness of the identified area of interest;
   b) selectively disqualifying the identified area of interest as being unlikely to be associated with the liquid product at least in part by processing the estimated thickness of the identified area of interest in combination with attenuation information derived from the X-ray image data.

32. An apparatus as defined in claim 30, wherein said processing unit is further programmed for:
   i. processing the X-ray image data to derive geometric information associated with the identified area of interest;
   ii. selectively disqualifying the identified area of interest for being unlikely to be associated with the liquid product at least in part based on the derived geometric information.

33. An apparatus as defined in claim 30, wherein said processing unit is further programmed for:
   i. processing the identified area of interest to derive density information associated with the identified area of interest;
   ii. selectively disqualifying the identified area of interest for being unlikely to be associated with the liquid product at least in part based on the derived density information.

34. An apparatus as defined in claim 30, wherein said processing unit is further programmed for:
   (1) processing the identified area of interest to determine whether it is likely to be associated with at least one object in a set of imposter objects;
   (2) selectively disqualifying the identified area of interest for being unlikely to be associated with the liquid product at least in part based on results obtained in (1).

35. An apparatus as defined in claim 34, wherein the set of imposter objects includes at least one object selected from the set consisting of CDs, Shoes, books and binders.

36. An apparatus as defined in claim 30, wherein identifying the area of interest includes:
   a) deriving compensated X-ray image data at least in part by compensating the X-ray image data for an amount of object induced X-ray attenuation resulting from X-rays travelling through an object in the piece of luggage, the object being unlikely to be part of the liquid product;
   b) using the compensated X-ray image data when identifying the area of interest in the image.

37. An apparatus as defined in claim 29, wherein said processing unit is further programmed for rendering a visual representation of the piece of luggage, the visual representation of the piece of luggage being derived at least in part based on the X-ray image data and the detection results and conveying to an operator a location in the piece of luggage corresponding to the liquid product.

38. An apparatus as defined in claim 37, wherein the location in the piece of luggage corresponding to the liquid product is conveyed by highlighting a portion of the visual representation of the piece of luggage.

39. A system suitable for performing security screening on luggage, said system comprising:
   a) an inspection device for performing an X-ray inspection on a piece of luggage using penetrating radiation to generate X-ray image data associated with the piece of luggage under inspection;
   b) an apparatus comprising:
      i. an input for receiving X-ray image data conveying an image of the piece of luggage and contents thereof, the X-ray image data being generated by scanning the piece of luggage with an X-ray scanner;
      ii. a processing unit programmed for processing the X-ray image data received at the input to detect if a liquid product is present in the piece of luggage, the liquid product being comprised of a container holding a body of liquid, wherein processing the X-ray image data includes detecting a liquid product signature in the X-ray image data;
      iii. an output for releasing detection results obtained by the processing unit;
   c) a display screen in communication with the output of said apparatus for visually conveying to an operator information derived at least in part based on the detection results released by the apparatus.

40. A system as defined in claim 39, wherein the inspection device is a multi-view X-ray machine.

* * * * *